United States Patent [19]

Shimizu et al.

[11] 4,386,158
[45] May 31, 1983

[54] METHOD OF PRODUCING PALATINOSE WITH IMMOBILIZED ALPHA-GLUCOSYL TRANSFERASE

[75] Inventors: Junichi Shimizu, Yokohama; Kazumasa Suzuki, Ayase; Yoshikazu Nakajima, Yamato, all of Japan

[73] Assignee: Mitsui Sugar Co., Ltd., Tokyo, Japan

[21] Appl. No.: 292,178

[22] Filed: Aug. 12, 1981

[30] Foreign Application Priority Data

Aug. 21, 1980 [JP] Japan ................. 55-113982

[51] Int. Cl.³ ............... C12P 19/18; C12P 19/12; C12N 11/02; C12N 11/10; C12N 11/04
[52] U.S. Cl. .................. 435/97; 435/100; 435/177; 435/178; 435/182
[58] Field of Search ............... 435/97, 100, 174, 177, 435/178, 179, 182

[56] References Cited

U.S. PATENT DOCUMENTS 3,733,205  5/1973  Shorers et al. ............ 435/174 X
4,138,292  2/1979  Chibata et al. ............ 435/179 X
4,257,884  3/1981  Lim ..................... 435/182 X
4,259,445  3/1981  Glass et al. .............. 435/178
4,334,027  6/1982  Klein et al. .............. 435/182 X
4,359,531  11/1982 Bucke et al. .............. 435/97

FOREIGN PATENT DOCUMENTS 1099  3/1979  European Pat. Off. ........... 435/100

OTHER PUBLICATIONS

Kierstan, et al., The Immobilization of Microbial Cells, Subcellular Organelles, and Enzymes in Calcium Alginate Gels, Biotech. and Bioeng., vol. XIX, 1977, (pp. 387–397).

*Primary Examiner*—David M. Nafe
*Attorney, Agent, or Firm*—Kane, Dalsimer, Kane, Sullivan and Kurucz

[57] ABSTRACT

Palatinose is produced from sucrose with an immobilized bacteria containing alpha-glucosyl transferase. The bacteria is immobilized by entrapping cells of the bacteria in calcium alginate gel granules and treating the granules with polyethyleneimine and glutaraldehyde. Palatinose is efficiently produced by packing the bacteria-containing granules in a column and passing a sucrose solution through the column at high velocity.

2 Claims, 1 Drawing Figure

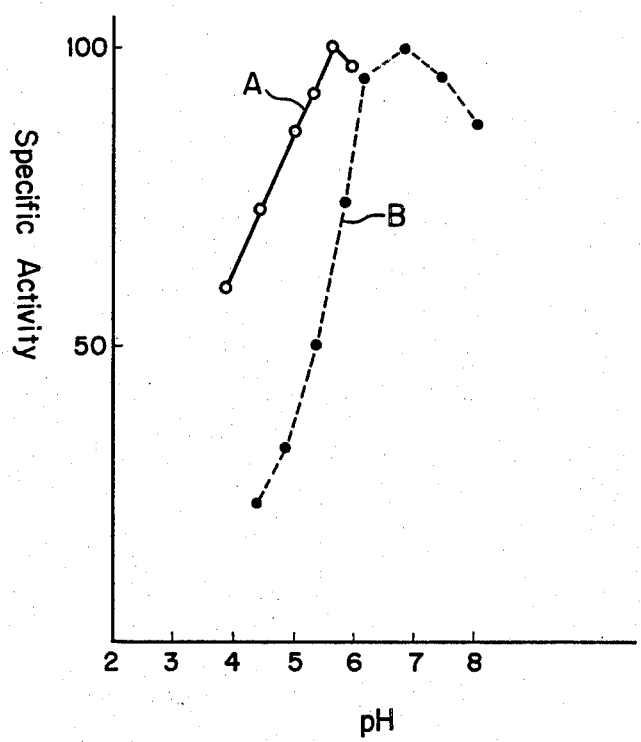

METHOD OF PRODUCING PALATINOSE WITH IMMOBILIZED ALPHA-GLUCOSYL TRANSFERASE

BACKGROUND OF THE INVENTION

1. Field of the invention

This invention relates to a method of producing palatinose for sucrose using immobilized α-glucosyl transferase.

2. Description of the Prior Art

Palatinose is a reducing disaccharide and it has been confirmed that palatinose is a natural component in honey and cane juice. The sweetness of it is about half of that of sucrose.

The molecular structure of palatinose is 6-O-α-D-glucopyranosyl-D-fructose in which glucose is bonded to fructose at 1,6-position. Palatinose is also called as isomaltulose.

In regard to a method of producing palatinose, a method is known wherein enzyme in a form of living or dead cells of Protaminobacter rubrum is added to an aqueous solution of sucrose to convert sucrose into palatinose and then the enzyme is separated from the solution as disclosed in West German Pat. No. 1,049,800. In this case, the separation of the enzyme is performed by centrifugal separation.

According to the technical level, α-glucosyl transferase forming palatinose from sucrose is produced by cultivating a certain kind of bacteria, i.e., *Protaminobacter rubrum, Serratis plymuthica*, etc., in the presence of sucrose. Since the enzyme associates with the cell of the bacteria, a mass of their cells itself can be used as an enzyme preparation.

Therefore, in the case of producing palatinose from sucrose, a mass of cells containing α-glucosyl transferase is added to an aqueous solution of sucrose in a concentration of 20–30% and the reaction is performed by stirring the mixture while controlling the mixture at a temperature of 20°–30° C. and a pH of about 7. The reaction period of time depends upon the amount of enzyme, the reaction temperature, etc., but, since the remaining amount of sucrose in the reaction mixture becomes very slight usually in about 20 hours after the addition of the cells, this point is defined as the end of the reaction, and then the cells are removed from the reaction mixture to provide an aqueous transparent solution of palatinose, which is purified by ion-exchange resin, etc., and then concentrated under reduced pressure to crystallize palatinose.

In the above procedure, the cells are removed from the reaction mixture usually by a centrifugal separation method, but, since the difference in specific gravity between the cells and the reaction mixture is small and also the size of the cells is very small, the separation efficiency is very poor and hence a very large installation is required for practicing the method, which gives a large problem in the case of practicing the method industrially.

SUMMARY OF THE INVENTION

As the result of various investigations on considering that the best manner for resolving this problem is to use immobilized α-glucosyl transferase, the inventors have found the useful method for immobilizing the enzyme and have finished the method of producing palatinose by the immobilized α-glucosyl transferase.

That is, according to this invention, there is provided a method of producing palatinose which comprises granulating cells of bacteria containing α-glucosyl transferase, which forms palatinose from sucrose, by entrapping in a calcium alginate gel, immersing the granules in a polyethyleneimine solution neutralized to a pH of 5.0–5.9 to make polyethyleneimine permeating into the granules until the concentration of polyethyleneimine in the gel becomes 0.5–1.5%, treating the granules with a glutaraldehyde solution containing glutaraldehyde in an amount of 1.5–5 times the amount of polyethyleneimine in the gel to form immobilized α-glycosyl transferase, and producing palatinose from sucrose using the immobilized α-glucosyl transferase.

BRIEF DESCRIPTION OF THE DRAWING

The FIGURE is a graph showing the pH characteristics of the enzyme activity.

DETAILED DESCRIPTION OF THE INVENTION

The inventors notice an entrapping method with calcium alginate gel at the first stage of the investigation. As is well known, this method can be very simply practiced by preparing an aqueous solution of a mixture of an enzyme and sodium alginate and adding dropwise the solution into an aqueous calcium chloride solution using a means such as an injector to gelatinize the mixture into granules. Although calcium alginate has such a fault that it is dissolved gradually at a pH higher than 5.8, the gel thereof has a high physical strength and hence can be easily used in either a fixed bed type reaction vessel or a fluidized bed type reaction vessel.

Thus, cells having α-glucosyl transferase activity obtained by inoculating Serratia plymuthica NCIB No. 8285 in an aqueous medium containing 5% sucrose, 3% corn steep liquor, 0.3% disodium hydrogenphosphate, and 0.2% sodium chloride and adjusted to an initial pH of 7, and cultivating aerobically and collected by centrifugal separation, was suspended in an aqueous 2% sodium alginate solution of about 40% by volume of the caltivated broth, the suspension was added dropwise to an aqueous 0.1 N calcium chloride solution using an injector followed by stirring for 2 hours, and then the granules thus formed were recovered by filtration and sufficiently washed with water. The above steps were all performed at temperatures below 25° C. so that α-glucosyl transferase was not inactivated.

When the granules thus obtained were added to a 30% (W/W) sucrose solution and while allowing to stand the mixture at 25° C., the reducing power thereof was measured with the passage of time, it was confirmed that the reducing power increased gradually. Also, by further analyzing it using a high speed liquid chromatography, it was proved that the increase of the reducing power was caused by the formation of palatinose. That is, by the calcium alginate gel entrapping method, α-glucosyl transferase could be granulated at any rate.

However, when the reaction mixture was filtered after almost all sucrose was converted into palatinose to recover the granules and the granules were sufficiently washed with water, added again to a 30% (W/W) sucrose solution, and allowed to stand 25° C., the increasing rate of the reducing power reduced below 1/10 at initial rate different from the first reaction. This is considered to be caused by the dissolution of enzyme into the reaction mixture. That is, the enzyme will become liable to liberate from the cells by some reason and on the other hand, the mesh of the lattice of calcium alginate gel will not be so fine as retaining the enzyme protein.

Thus, it has been found that although α-glucosyl transferase can be granulated by the calcium alginate gel entrapping method, α-glucosyl transferase cannot be immobilized.

Therefore, the inventors considered that if glutaraldehyde as a crosslinking reagent, which was widely used for immobilizing enzyme was applied to the granules obtained by the above-described method, complicated crosslinking bonds would form on the cells entrapped by the gel and thus α-glucosyl transferase would become reluctant to release and the inventors investigated on the conditions for the glutaraldehyde treatment.

To 100 ml each of aqueous glutaraldehyde solutions at concentrations of 0%, 0.025%, 0.05%, 0.1% and 0.5% were added 30 g of the granules of the enzyme included by the calcium alginate gel prepared under the same conditions as described above and after treating the mixture for 30 minutes at 25° C., the granules were recovered by filtration and washed with water in each case. The granules thus obtained was added to 100 g of a 33.3% (W/W) sucrose solution and the reaction mixture was incubated for 20-23 hours at 25° C. After the reaction was over, the granules were recovered by filtration, washed sufficiently with water, and added to 100 g of a 33.3% (W/W) sucrose solution to perform the second reaction. Thus, a series of reactions was carried out. At the initiation of each reaction, the pH was adjusted to 6.5-7.0, but the pH was reduced to 5.0-5.5 in 2 hours and to 4.3-4.8 in 20 hours. In each reaction a small amount (2-5 g) of the supernatent of the reaction mixture was sampled at the time point of 2 hours after the initiation of the reaction, the solid content was measured by a refractometer and reducing sugar was measured by a Shaffer-Somogyi micromethod, and then the conversion rate of sucrose was determined from these values.

The results of the test are shown in Table 1. From the results, it is understood that the most suitable concentration of a glutaraldehyde solution is 0.1% in the experiment and when the concentration of the solution is 0.025% or 0.05%, the enzyme is insufficiently immobilized to reduce the activity quickly, while when the concentration is 0.5%, the enzyme is greatly inactivated by the immobilizing treatment. However, since the reduction in activity is fast even by using a 0.1% glutaraldehyde solution which gave the best result in the above-described experiment, it was found that the immobilized enzyme could not be obtained with high productivity by the glutaraldehyde treatment only.

Polyethyleneimine has a property of being gelled by causing a reaction with glutaraldehyde, but since the gel is poor in physical strength, it is unsuitable to use polyethyleneimine alone for immobilized enzyme. The inventors have discovered that when the polyethyleneimine is gelled by the treatment with glutaraldehyde after permeated into the calcium alginate gel, a gel having high enzyme retention power and high physical strength is formed by compensating the faults of the two kinds of gels with each other, and the invention has been accomplished based on the above discovery.

Then, the invention will be explained in detail by referring to the embodiments while comprising wich comparison examples.

Granules of the enzyme entrapped in a calcium alginate gel were prepared by the same manner as described above, and 30 g each of the granules were used for preparing immobilized enzyme. In addition, it is preferred that the size of the granules be 0.5-5 mm, in particular 1-3 mm. in diameter.

Since a polyethyleneimine solution shows a strong alkaline property and dissolves calcium alginate, the solution was neutralized to pH 5.0-5.8 with hydrochloric acid before use. The amount of the polyethyleneimine solution was 30 g and the concentration was twice the predetermined concentration of the solution to be permeated. In other words, polyethyleneimine solutions of concentrations of 1%, 2% and 3% were used for permeate it in the gel at concentrations of 0.5%, 1%, and 1.5%, respectively. After immersing the granules in the polyethyleneimine solution for about 10 minutes, the granules were recovered by suction filtration, added, without being washed with water, to 100 ml of a glutaraldehyde solution of a define concentration, and treated therein for 30 minutes. Thereafter, the granules were recovered by filtration, sufficiently washed with water, repeatedly used for the reaction as in the above-described experiment, and the changes of the sucrose conversion rate during 2 hours were pursued. It was confirmed that about 80-90% according to temperature condition of the converted sucrose was converted into palatinose.

The results of the aforesaid experiment on the effect of using polyethyleneimine together are shown in Table 2. As a comparison example of the case without using polyethyleneimine, the data on Sample No. 5 shown in Table 1 were also shown in Table 2. Since polyethyleneimine combined with glutaraldehyde, a relatively large amount of glutaraldehyde was required.

As in the case of Sample No. 10, sufficient immobilizing effect is not obtained by using 0.1% glutaraldehyde and as in the case of Sample No. 9, the immobilizing extent is still insufficient even by using 0.2% glutaraldehyde.

In Sample No. 7, 1% polyethyleneimine was absorbed in the gel and the gel was treated with 0.5%

TABLE 1

| | Experimental results on the glutaraldehyde treatment effect for enzyme entrapped in calcium alginate gel | | | | | | | | |
|---|---|---|---|---|---|---|---|---|---|
| Sample no. | Concn. of glutaraldehyde (%) | Sucrose conversion rate (%) after 2 hours | | | | | | | |
| | | once | twice | three times | four times | five times | six times | seven times | eight times |
| 1 | 0 | 62.9 | 8.4 | 0 | — | — | — | — | — |
| 2 | 0.025 | 49.4 | 52.6 | 30.1 | 16.7 | 6.3 | 3.4 | — | — |
| 3 | 0.05 | 43.0 | 49.9 | 38.7 | 22.0 | 18.2 | 12.6 | 9.2 | 6.6 |
| 4 | 0.1 | 31.0 | 43.1 | 38.4 | 32.7 | 29.4 | 25.8 | 22.5 | 20.0 |
| 5 | 0.5 | 7.6 | 15.0 | 14.5 | 16.1 | 10.5 | 10.3 | 9.4 | 7.5 | glutaraldehyde, and in this case the initial activity was high and stable. In Sample No, 8, the absorbed amount of polyethyleneimine was 1.5% of the gel and the concentration of glutaraldehyde was 1%, and in this case the initial activity was a little low but the stability was very high. Thus, considering that the presumed amount of the concentration of polyethyleneimine in the gel includes a considerable error, the optimum conditions have been found to be that the concentration of polyethyleneimine is in a range of 0.5-1.5% based on the amount of the gel and the concentration of the glutaraldehyde solution is in a range of 0.5-1.0%. If the concentration of polyethyleneimine is higher than the aforesaid range, the diffusion resistance of sucrose and the reaction product increases undesirably and if the concentration is lower than the aforesaid range, the stability for immobilizing becomes poor.

However, quantitative ratio of polyethyleneimine and glutaraldehyde is important and it has been found that good result is obtained when the amount of glutaraldehyde is in a range of 1.5 times to 5 times that amount of polyethyleneimine.

In the case of Sample No. 7, the amount of polyethyleneimine in the gel was in a range of 0.15-0.3 g, while the amount of glutaraldehyde used was 0.5 g and in the case of Sample No. 8, the amount of polyethyleneimine was 0.23-0.45 g, while the amount of glutaraldehyde used was 1.0 g.

was sought, and the numbers of usage until the activity became 50% of the maximum activity and 25% of the maximum activity were deduced. Since the maximum activity frequently appears after the second time, the number of usage until the activity becomes 25% of the maximum activity is not always twice the number of usage until the activity becomes 50% of the maximum activity. The productivity was shown by the sum of the value of the specific activity of each usage. The results are summarized in Table 3.

TABLE 3

Comparison of usable number and productivity:

| Sample no. | Immobilizing condition (A)* | Immobilizing condition (B)* | Number of Usable times 50* | Number of Usable times 25* | Productivity 25* |
|---|---|---|---|---|---|
| 1 | 0 | 0 | 1 | 1 | 100 |
| 2 | 0 | 0.025 | 2 | 4 | 189 |
| 3 | 0 | 0.05 | 3 | 5 | 222 |
| 4 | 0 | 0.1 | 6 | 10 | 327 |
| 5 | 0 | 0.5 | 8 | 13 | 125 |
| 6 | 0.5 | 0.5 | 11 | 19 | 225 |
| 7 | 1.0 | 0.5 | 19 | 36 | 746 |
| 8 | 1.5 | 1.0 | 36 | 70 | 749 |
| 9 | 1.0 | 0.2 | 7 | 12 | 360 |
| 10 | 1.0 | 0.1 | 3 | 6 | 197 |

(A): polyethyleneimine (%)
(B): glutaraldehyde (%)
(50%): up to 50% activity
(25%): up to 25% activity.

TABLE 2

Experimental results on the effect of using polyethyleneimine together with glutaraldehyde

| Sample no. | Immobilizing condition (A)* | Immobilizing condition (B)* | Sucrose conversion rate (%) in 2 hours once | twice | three times | four times | five times | six times | seven times | eight times |
|---|---|---|---|---|---|---|---|---|---|---|
| 5 | 0 | 0.5 | 7.6 | 15.0 | 14.5 | 16.1 | 10.5 | 10.3 | 9.4 | 7.5 |
| 6 | 0.5 | 0.5 | 11.0 | 17.7 | 18.1 | 17.3 | 16.6 | 15.4 | 12.3 | 12.0 |
| 7 | 1.0 | 0.5 | 24.8 | 30.4 | 30.1 | 29.8 | 26.7 | 26.7 | 26.0 | 24.5 |
| 8 | 1.5 | 1.0 | 11.4 | 18.3 | 18.0 | 18.1 | 18.3 | 17.6 | 16.3 | 16.4 |
| 9 | 1.0 | 0.2 | 36.3 | 40.0 | 35.5 | 33.3 | 28.4 | 24.9 | 22.5 | 20.0 |
| 10 | 1.0 | 0.1 | 41.3 | 35.4 | 34.2 | 22.3 | 15.4 | 13.7 | 11.2 | 9.2 |

(A): The concentration of polyethyleneimine in the gel after immersing the gel in polyethyleneimine solution.
(B): The concentration of glutaraldehyde solution.

The effect of using polyethyleneimine together with glutaraldehyde is already clear from the data shown in Table 2, but for further clarifying the effect, the number of usage until the activity reduces by half and that until the activity reduces by 75% are determined from the data in Table 1 and Table 2 as well as the comparative value of the productivity until the activity reduces by 75% is calculated as follows:

The reaction is assumed to occur according to rate equation (1) of a first order reaction:

$$K = -1/t \log(1-x) \quad (1)$$

wherein
K: reaction rate constant
t: reaction time
x: conversion rate of sucrose.

On considering that in equation (1), K is in proportion to the apparent enzyme activity in the reaction system and t is constant, the apparent enzyme activity is in proportion to $-\log(1-x)$ and hence the initial value of $-\log(1-x)$ of Sample No. 1 is defined to be 100 as standard and then the specific activity of each sample per each use was calculated. Then, the reduction rate of the activity of each enzyme is assumed to be constant, the activity was plotted on a semilog graph of which the axis of abscissa for the using number and the axis of ordinate stands for the specific activity, a regression The results in Table 3 show clearly that the immobilizing treatment in the above-described optimum condition improve greatly the productivity.

Furthermore, in another embodiment of this invention for producing palatinose, in a recycle system of supplying a sucrose solution to a column packed with the immobilized α-glucosyl transferase obtained in the aforesaid method from a storage tank through pump and returning the reaction mixture from the outlet of the column into the storage tank, the pH in the storage tank and pH of the recycling solution in pipe lines are adjusted.

Now, the properties of the immobilized α-glucosyl transferase obtained in this invention will be described.

As described above, calcium aliginate is dissolved gradually in a solution at pH above 5.8 and hence the reaction must be performed at a pH below 5.8. For example, if the pH of the reaction mixture is neutralized to 7.0, the pH reduces quickly and is stabilized when the pH becomes below 5.8.

The FIGURE is a graph showing the pH characteristics of the enzyme activity measured using a 30% (W/W) sucrose solution dissolved in a 0.02 M acetic acid·calcium acetate buffer solution. In the figure a solid line (A) stands for the immobilized enzyme and a dotted line (B) stands for a liberate cellular enzyme. The active pH range is shifted to an acid side as compared to the liberated cellular enzyme but it is clear that the pH during reaction is preferably kept as high as possible in a range of not reducing the stability of the gel. Therefore, the pH of the reaction mixture is maintained at 5.0–5.8, preferably at about 5.5.

Then, the influence of temperature is explained. The immobilized enzyme by the method of this invention immersed in a 30% (W/W) sucrose solution dissolved in a 0.02 M acetic acid.calcium acetate buffer solution at pH 5.5 was maintained for 30 minutes at a definite temperature and thereafter the immobilized enzyme was recovered by filtration and sufficiently washed with water. Then, when the immobilized enzyme was reacted in a sucrose solution having the same composition as above for 2 hours at 30° C. and then the remaining activity thereof was measured, the reduction in the activity did not occur at 30° C. but the reduction in the activity was clearly observed at temperatures below 35° C. Therefore, as in the case of using the liberated cellular enzyme, it is necessary to use at temperatures below 30° C.

In the case of using practically the enzyme by this invention, a reaction bath of stirring system can be, as a matter of course, used, but for preventing destroying of the granules as well as possible, it is better to use a column packed with the granules, preferably to use as a fixed bed-type column. The pressure loss in the column is very small and a considerably high linear velocity can be employed. If the retention time in the column is prolonged, the pH reduces to reduce the apparent activity of enzyme, and hence a recycle system with a shortened retention time is employed and the pH of the recycling system outside the column is adjusted to about 5.5. This is considered to be the most suitable means for using the enzyme of this invention. Also, the immobilized enzyme particles or granules of a comparatively large amount as compared with the amount of a solution to be treated are packed in a column and the solution to be treated is passed once through the column, thereby the greater part of sucrose can be converted into palatinose. When more than 98% of sucrose is converted into the products, the reaction is stopped and a transparent liquid obtained through a simple screen can be directly sent to the subsequent step. Thus, there is no trouble as in the case of using liberated cellular enzyme.

Furthermore, this enables that the initial sucrose concentration of the reaction mixture can be increased over the case of using conventional liberated cells in an allowable range by the solubulity of palatinose which is the product. Since palatinose is dissolved in water of about 1.5 times the weight thereof at 30° C., the initial sucrose concentration may be about 40% (W/W). Thus, the cost required for concentration of the liquid in a crystallization step can be greatly reduced.

Also, in the case of obtaining the immobilized enzyme having higher activity than those in the examples explained above by the method of this invention, the amount of the enzyme entrapped in the calcium alginate gel may be increased, which can be very easily attained.

Then, the embodiments of this invention will be explained below in more detail and practically by the following examples.

EXAMPLE 1

In a 30 liter jar fermenter was placed 15 liters of a culture medium of pH 7 containing 5% sucrose, 3% corn steep liquor, 0.3% disodium hydrogenphosphate, and 0.2% sodium chloride followed by sterilization and after inoculating Serratia plymuthica NCIB No. 8285, the fermentation was carried out at a temperature of 28° C. for 16 hours at an aeration rate of 7.5 liters/min., and a stirring rate of 400 r. p. m. to provide a cultured material having a high α-glucosyl transferase activity, which was separated by centrifugal separation to provide 2.5 liters of a slurry of cells containing the enzyme.

The cellular slurry thus obtained was mixed well with 2.5 liters of an aqueous solution of 4% sodium alginate, the mixture was placed in a cylindrical extruder equipped with a die having a number of pores of 0.6 mm diameter at the end head, and the mixture was extruded downward through the die by applying air pressure. Below the extruder was placed a 20 liter vessel containing 10 liters of an aqueous 0.15 M calcium chloride solution and while stirring the solution with a stirrer, the liquid drops of the mixture falling through the die were added to the solution. The extrusion was finished after 10 minutes and thereafter, the calcium chloride solution was stirred for 2 hours to strengthen the physical properties of granules formed in the solution. Thereafter, the granules were recovered by filtration and washed well with water. The weight of the granules obtained was 5 kg.

After diluting 270 g of 30% polyethyleneimine with about 3 liters of water, the solution obtained was neutralized to pH 5.5 with diluted hydrochloric acid and then the total amount thereof was adjusted to 4 kg. The whole amount of the above-described granules were added to the solution and after stirring slowly, the granules were recovered by filtration. It was estimated by the solid content analysis of the waste solution that about 20 g of polyethyleneimine had been permeated in the granules. Thus, 10 liters of a 0.5% glutaraldehyde solution containing 50 g of glutaraldehyde which was 2.5 times the estimated amount was prepared, the granules containing polyethyleneimine were added to the solution and after stirring mildly for 30 minutes, the granules were recovered by filtration and sufficiently washed with water.

The above steps were all performed at about 25° C.

The amount of the immobilized glucosyl transferase thus obtained was 3.3 kg and the enzyme was packed in a 5 liter column.

In 9 kg of water was dissolved 6 kg of fine granulated sugar and after adjusting the temperature of the solution to 25° C., the solution was recycled through the column by supplying the solution to the column at a rate of 50 liters/hr. by means of a pump and returning the solution from the lower outlet of the column to the original vessel. Since the pH of the solution during recycling reduced gradually, the pH of the solution was adjusted to about 5.5 with an aqueous sodium hydroxide solution using an automatic pH controller. When the recycling was continued for 22 hours, more than 98% of sucrose was decomposed to form palatinose.

Thus, the sugar solution was discharged and a second reaction was started using the fresh sugar solution. The amount of the sucrose solution was same until the third reaction but thereafter, the amount of the sucrose solution was gradually reduced in accordance with the reduction in activity. It took 25 days until the treating amount of sucrose per day reduced by half. During this period, the amount of sucrose treated amounted to 110 kg. When the experiment was further repeated, it took 48 days until the activity became ¼ of the initial activity and the treated of sucrose was 160 kg.

EXAMPLE 2

A 6% sodium alginate solution was prepared and 1.25 liters of the solution was mixed with 2.5 liters of a cellular slurry prepared as in Example 1. Then, by dropping the mixture through an extruder as described in Example 1 into 8 liters of a 0.15 M calcium chloride solution, 3 kg of granules were obtained.

After adjusting the pH of 3 liters of a 2.5% polyethyleneimine solution to 5.5, the granules were immersed in the solution for 10 minutes, thereby 30 g of polyethyleneimine permeated into the granules. thus, the granules were treated for 30 minutes with 9 liters of a 1% glutaraldehyde solution containing 90 g of glutaraldehyde which was 3 times the amount of the polyethyleneimine and then the granules were recovered by filtration and washed with water to provide 2.5 kg of immobilized α-glucosyl transferase.

The immobilized enzyme was packed in a column and was used as in Example 1. In this case, the amount of sucrose treated in one day was 5 kg at the beginning but even after 25 days, the column kept a treating faculty of 3.0 kg/day. The amount of sucrose treated during 25 days was 93 kg and it took about 50 days until the activity became ¼ of the initial activity. The amount of sucrose treated was 185 kg.

EXAMPLE 3

Protaminobacter rubrum CBS 57477 was cultivated using a culture medium containing 5% sucrose, 3% corn steep liquor, 0.5% yeast extract, 0.3% disodium hydrogenophosphate, and 0.2% sodium chloride for 20 hours at an initial pH of 7.0, a temperature of 28° C., an aeration rate of ¼ v. v. m., and a stirring rate of 300 r. p. m. to provide 15 liters of a cultured material.

The cultured material was subjected to a centrifugal separation to provide 3 liters of a cellular slurry, which was well mixed with 1.5 liters of a 4% sodium alginate solution, the mixture was dropped in a calcium chloride solution as in Example 1 to form granules, and the granules were washed with water. Then, after permeating polyethyleneimine into the granules, the granules were treated with a glutaraldehyde solution to provide 2.6 kg of fixed α-glucosyl transferase, which was packed in a 5 liter column.

A solution of sucrose dissolved in a 0.01 M acetic acid.calcium acetate solution at a concentration of 30% (W/W) was passed through the solumn at a temperature of 25° C. and a flow rate of 2.5 liters/hr. The proportion of sucrose in the effluent analyzed with 0.5%, which showed that the greater part of sucrose was converted into palatinose in the column. When the column was used for 30 days under the same conditions as above, the content of sucrose in the effluents was in a range of 0.5–1.5%. The amount of sucrose treated in 30 days was 540 kg.

EXAMPLE 4

In a 200 milliliter column was packed 100 g of the immobilized α-glucosyl transferase obtained as in Example 3, 2 liters of a 30% (W/W) sucrose solution was passed through the column at a rate of 500 ml/hr., and recycled as in Example 1. An automatic pH controller was equipped to the vessel for the sucrose solution and the pH was adjusted to 5.5±0.1 using a saturated calcium hydroxide solution. The temperature of the reaction system was kept at 25° C. Since the concentration of sucrose in the reaction mixture reduced below 0.5% after 20 hours, the sucrose solution was renewed and the reaction was started again. Thus, the reaction was carried out 20 times in such a manner but no remarkable change was observed about the enzyme activity of the column.

EXAMPLE 5

Without using the column as in Example 4, 100 g of the immobilized enzyme as in Example 4 was added to 2 liters of a sucrose solution and when the reaction was continued for 20 hours with stirring while adjusting the pH to 5.5 and the temperature to 25° C., the concentration of sucrose became 0.3%. The enzyme was recovered by filtration and used in the subsequent reaction. Thus, the enzyme was used 20 times but no remarkable change was observed about the enzyme activity.

What is claimed is:

1. A method of producing palatinose which comprises forming calcium alginate gel granules having entrapped therein cells of bacteria containing α-glucosyl transferase, which forms palatinose from sucrose immersing the granules in a polyethyleneimine solution neutralized to a pH of 5.0–5.9 to permeate polyethyleneimine into the granules until the concentration of polyethyleneimine in the gel becomes 0.5–1.5%, treating the granules with a glutaraldehyde solution containing glutaraldehyde in an amount of 1.5–5 times the amount of polyethyleneimine in the gel to form immobilized α-glucosyl transferase, and producing palatinose from sucrose using the immobilized α-glucosyl transferase.

2. A method of producing palatinose which comprises forming calcium alginate gel granules having entrapped therein cells of bacteria containing α-glucosyl transferase, which forms palatinose from sucrose immersing the granules in a polyethyleneimine solution neutralized to a pH of 5.0–5.9 to permeate polyethyleneimine into the granules until the concentration of polyethyleneimine in the gel becomes 0.5–1.5%, treating the granules with a glutaraldehyde solution containing glutaraldehyde in an amount of 1.5–5 times the amount of polyethyleneimine in the gel to form immobilized α-glucosyl transferase, packing the immobilized α-glucosyl transferase in a column, and recycling a sucrose solution from a storage tank through the column while adjusting the pH of the recycling solution in the tank or in pipe lines through which the sucrose solution passes from the storage tank to the column or from the column to the storage tank during recycling.

* * * * *